(12) United States Patent
Okano et al.

(10) Patent No.: US 7,785,596 B2
(45) Date of Patent: Aug. 31, 2010

(54) METHODS FOR ENHANCING SURVIVAL AND/OR PROLIFERATION OF NEURAL STEM CELLS AND NEURITE EXTENSION ENHANCERS THEREFOR PHARMACEUTICAL COMPOSITIONS CONTAINING NEURAL STEM CELLS ASSAY METHODS AND SCREENING METHODS

(75) Inventors: Hideyuki Okano, Tokyo (JP); James Hirotaka Okano, Tokyo (JP); Masanori Sakaguchi, Tokyo (JP); Hidehiro Mizusawa, Tokyo (JP); Satoru Ishibashi, Tokyo (JP)

(73) Assignee: Keio University, Tokyo (JP)

( * ) Notice: Subject to any disclaimer, the term of this patent is extended or adjusted under 35 U.S.C. 154(b) by 132 days.

(21) Appl. No.: 10/571,277

(22) PCT Filed: Sep. 8, 2004

(86) PCT No.: PCT/JP2004/013043

§ 371 (c)(1),
(2), (4) Date: Mar. 9, 2006

(87) PCT Pub. No.: WO2005/026343

PCT Pub. Date: Mar. 24, 2005

(65) Prior Publication Data

US 2007/0098701 A1     May 3, 2007

(30) Foreign Application Priority Data

Sep. 9, 2003    (JP)   ............................ 2003-317379

(51) Int. Cl.
*C12N 5/10*    (2006.01)
*C12N 15/74*    (2006.01)
*C12N 15/75*    (2006.01)
*C12N 15/82*    (2006.01)

(52) U.S. Cl. .................... 424/158.1; 435/355; 435/366; 435/368; 435/377

(58) Field of Classification Search .............. 424/158.1; 435/355, 366, 368, 377
See application file for complete search history.

(56) References Cited

U.S. PATENT DOCUMENTS 6,436,389 B1 * 8/2002 Gage et al. ................. 424/85.1
6,890,531 B1 * 5/2005 Horie et al. ............... 424/130.1

FOREIGN PATENT DOCUMENTS

| EP | 1 122 311 A1 | 8/2001 |
| EP | 1 302 533 A1 | 4/2003 |
| JP | 2002-325571 | 11/2002 |
| JP | 2002-371005 | 12/2002 |
| WO | WO 00/06724 | 2/2000 |
| WO | WO 01/88100 A1 | 11/2001 |
| WO | WO 02/099102 | 12/2002 |

OTHER PUBLICATIONS

Wells et al., Identification of an autocrine negative growth factor: mouse beta-galactoside-binding protein is a cytostatic factor and cell growth regulator.Cell. Jan. 11, 1991;64(1):91-7.*

Johansson CB et al., Neural stem cells in the adult human brain. Exp Cell Res. Dec. 15, 1999;253(2):733-6.*

Galli R,et al., Neural stem cells: an overview Circ Res. Apr. 4, 2003;92(6):598-608.*

Horie, H. et al., "Galectin-1 Regulates Initial Axonal Growth in Peripheral Nerves After Axotomy," The Journal of Neuroscience, vol. 19, No. 22, pp. 9964-9974, (Nov. 15, 1999).

Inagaki, Y. et al., "Oxidized Galectin-1 Promotes Axonal Regeneration in Peripheral Nerves but Does Not Possess Lectin Properties," Eur. J. Biochem., vol. 267, pp. 2955-2964, (2000).

Horie, H. et al., "Identification of Oxidized Galectin-1 as an Initial Repair Regulatory Factor after Axotomy in Peripheral Nerves," Neuroscience Research, vol. 38, pp. 131-137, (2000).

Brent Reynolds et al., "Generation of Neurons and Astrocytes From Isolated Cells of the Adult Mammalian Central Nervous System", Science, American Association for the Advancement of Science, vol. 255, No. 5052, Mar. 1992, pp. 1707-1710.

(Continued)

*Primary Examiner*—Maria Leavitt
(74) *Attorney, Agent, or Firm*—Finnegan, Henderson, Farabow, Garrett & Dunner, L.L.P.

(57) ABSTRACT

Methods for enhancing survival and/or proliferation of neural stem cells and pharmaceutical compositions containing neural stem cells prepared by such methods, together with methods for assaying factors enhancing survival and/or proliferation of neural stem cells and methods for screening for such factors.

Either Galectin-1 is overexpressed in neural stem cells or neural stem cells are cultured in a liquid medium containing Galectin-1. Pharmaceutical compositions containing Galectin-1-overexpressing neural stem cells and pharmaceutical composition containing Galectin-1, prepared by the aforementioned methods, improve higher cerebral functions damaged by cerebral ischemia. Further, by seeding neural stem cells at clonal concentrations and determining whether the seeded neural stem cells are capable of proliferating in an assay medium to be assayed, whether the factor enhances survival and/or proliferation of neural stem cells is assayed and a factor enhancing survival and/or proliferation of neural stem cells are identified using this assay method.

12 Claims, 8 Drawing Sheets

OTHER PUBLICATIONS

Stefano Pluchino et al., "Injection of Adult Neurospheres Induces Recovery in a Chronic Model of Multiple Sclerosis", Nature Publishing Group, vol. 422, Apr. 2003, pp. 688-694.

Kimberly Walsh et al., "Human Central Nervous System Tissue Culture: A Historical Review and Examination of Recent Advances", Neurobiology of Disease, vol. 18, No. 1, Feb. 2005, pp. 2-18.

* cited by examiner

METHODS FOR ENHANCING SURVIVAL AND/OR PROLIFERATION OF NEURAL STEM CELLS AND NEURITE EXTENSION ENHANCERS THEREFOR PHARMACEUTICAL COMPOSITIONS CONTAINING NEURAL STEM CELLS ASSAY METHODS AND SCREENING METHODS

CROSS REFERENCE TO RELATED APPLICATIONS

This application claims the benefit of priority to Japan Patent Application No. 2003-317379, filed on Sep. 9, 2003, which is incorporated herein by reference.

TECHNICAL FIELD

The present invention relates to methods for enhancing survival and/or proliferation of neural stem cells and neurite extension, and pharmaceutical compositions containing neural stem cells, assay methods, and a screening method.

BACKGROUND ART

Regeneration of the injured central nervous system is difficult, but it has been reported in animal experiments that transplantation of embryo tissues, especially of neural stem cells, is effective. However, to obtain neural stem cells sufficient for therapy, many donations of aborted embryos are required. Moreover, since use of embryos is an ethical issue, practical clinical application of neural stem cells is difficult.

Thus, as a candidate of a transplantation material replacing neural stem cells directly isolated from embryos, neural stem cells that have been cultured and have proliferated in vitro have been a focus of attention. Neural stem cells are undifferentiated cells with self-replication ability and pluripotency. Since they proliferate unlimitedly by in vitro culture, they enable supply of a sufficient number of donor cells.

As a method for growing neural stem cells in vitro, the neurosphere method reported by Weiss et al. (Science 255, 1707-1710, 1992) is commonly used. Many examples of successful treatments have been reported, which were performed by transplanting neural stem cells proliferated through the neurosphere method to patients especially with intractable diseases, such as cerebral ischemia and neural degenerative diseases (Nature 422, 688-694, 2003).

DISCLOSURE OF THE INVENTION

Problems to be Solved by the Invention

Neural stem cells can proliferate in vitro in the neurosphere method. Under this culture condition, however, their proliferation rate is sometimes very slow compared with other cells, which is one of the characteristics of neural stem cells. Therefore, in order to obtain the number of neural stem cells enough for use in actual transplantation, it is necessary to improve the proliferation rate. Furthermore, for transplanted neural stem cells to differentiate into neurons and function as such in a patient's body, the more active neurite extension is, the more favorable they are.

Thus, an object of the present invention is to provide methods for enhancing survival and/or proliferation of neural stem cells, pharmaceutical compositions containing neural stem cells prepared by such methods, and methods for enhancing neurite extension when differentiation of neural stem cells is induced.

When neural stem cells that have made to proliferated in the neurosphere method are transplanted to patients especially with intractable diseases, such as cerebral ischemia and neural degenerative diseases, if the neural stem cells are derived from an individual other than the patient, some measures should be taken for rejection in the recipient. It is therefore preferable to make neural stem cells of the patient him/herself proliferate on the spot.

Thus, another object of the present invention is to provide neural stem cells proliferation enhancers and SVZ astrocytes proliferation enhancers for enhancing proliferation of neural stem cells and SVZ astrocytes, respectively; and methods for enhancing proliferation of neural stem cells and SVZ astrocytes for enhancing proliferation of neural stem cells and SVZ astrocytes, respectively.

Means for Solving the Problem

The inventors found that the conditioned media of the OP9 cells and neurospheres (which are hereinafter called OP9CM and NSF-CM, respectively) have activity that maintains survival and proliferation of neural stem cells at low densities. Accordingly, an active OP9CM was compared (N=4) with an inactive OP9CM using a quantitative mass spectrometer (Protein chip:CIPHERGEN), and a list of molecular weights of the molecules exhibiting difference in expression between the conditioned media was made. One molecule with the highest reproducibility was chosen from the list, and fragmentary amino acid sequences were determined using a double-focusing mass spectrometer (Q star: ABI). It was found that the molecule was Galectin-1.

Galectin-1 is a lectin that binds to beta-galactoside, known to be present in the cytoplasm as well as outside the cells. Expression of Galectin-1 in OP9CM and NSF-CM was examined by Western blotting and Galectin-1 was certainly detected in these conditioned media. Then, the activity of Galectin-1 was inhibited by forced expression of the antisense cDNA of Galectin-1 and neural stem cell proliferation was found to be markedly suppressed. Further, thiodigalactoside (10 mM), which can inhibit Galectin-1 activity by competing with sugar, was added to NSF-CM and the activity that maintains survival and proliferation of neural stem cells at low densities was inhibited.

These results suggest that the above-mentioned activity in OP9CM and NSF-CM originates in the sugar-binding activity of Galectin-1. It was clarified that either overexpressing this Galectin-1 in neural stem cells or adding Galectin-1 into the culture medium of neural stem cells enables enhancement of viability and/or the growth ratio of neural stem cells. The present invention has thus been accomplished.

In the present invention thus accomplished, a method for enhancing survival or proliferation, or both, of neural stem cells in a liquid medium includes the step of overexpressing Galectin-1 or Galectin-3 in the neural stem cells. In another embodiment, neural stem cells may be cultured in a liquid medium containing Galectin-1 or Galectin-3.

As used herein, the term "Galectin-1 (or 3)," when simply used, is intended to include both wild-type Galectin-1 (or -3) and mutant Galectin-1 (or -3) with β-galactoside-binding activity.

In these embodiments, culture media may contain the neural stem cell-conditioned medium, especially the neurosphere-conditioned medium or the OP9 cell-conditioned medium. In addition, Galectin-1 or Galectin-3 may be derived from these conditioned media.

The pharmaceutical composition according to the present invention contains as an active ingredient a neural stem cell in which Galectin-1 or Galectin-3 is overexpressed, and improves a higher brain function damaged by brain ischemia. The higher brain function may be either motor function or sensory function.

Further, the therapeutic method according to the present invention improves a symptom derived from brain ischemia by transplanting in vivo a neural stem cell in which Galectin-1 or Galectin-3 is forcibly expressed in a mammal other than a human. The symptom can be, for example, a higher brain dysfunction such as motor dysfunction, or sensory dysfunction. This method of treatment can also be applied to a human.

Further, the method for enhancing neurite extension when differentiation of a neural stem cell is induced in vitro according to the present invention includes the step of overexpressing Galectin-1 in the neural stem cell. This method may also be applied to an animal.

Further, the enhancer for enhancing in vivo proliferation of a neural stem cell in a vertebrate according to the present invention contains Galectin-1 or Galectin-3 as an active ingredient.

Further, in the method for enhancing in vivo proliferation of a neural stem cell in a normal vertebrate according to the present invention, Galectin-1 or Galectin-3 is injected into the brain. This method can also be applied to a human and a vertebrate other than a human as long as it is a normal animal.

Further, in the method for enhancing in vivo proliferation of a neural stem cell in a vertebrate other than a human according to the present invention, Galectin-1 or Galectin-3 may be injected into the brain. This method is intended for a vertebrate with a neurological disorder, thereby requiring neurotherapy, especially for a vertebrate other than a human. However, it can also be applied to a human.

Further, the enhancer for enhancing in vivo proliferation of an SVZ astrocyte in a vertebrate according to the present invention contains Galectin-1 or Galectin-3 as an active ingredient.

Further, in the method for enhancing in vivo proliferation of an SVZ astrocyte in a normal vertebrate according to the present invention, Galectin-1 or Galectin-3 is injected into the brain. This method can be applied to a human and a vertebrate other than a human as long as it is a normal animal.

Further, in the method for enhancing in vivo proliferation of an SVZ astrocyte in a vertebrate other than a human according to the present invention, Galectin-1 or Galectin-3 may be injected into the brain. This method is intended for a vertebrate with a neurological disorder, thereby requiring neurotherapy, especially for a vertebrate other than a human. However, it can also be applied to a human.

To date, techniques for clonally culturing neural stem cells have not been known, nor has it even been clear whether or not they can be cultured clonally. The technique for clonally culturing neural stem cells has now been established by the present inventors. Thus, the following assay methods and screening methods have been accomplished.

The method for assaying the activity of a target substance added into a liquid medium, which enhances survival or proliferation, or both, of a neural stem cell includes the step of seeding a neural stem cell at a clonal density, using an assay medium made by adding the substance to a basal medium incapable of inducing proliferation of a neural stem cell at a clonal density and the step of determining whether or not the seeded neural stem cell can proliferate in the assay medium. This neural stem cell may be the one selected using CD15+ as an index. Seeding may be performed at the clonal density by placing one neural stem cell per well of a culture plate.

The screening method for identifying an active substance with activity that enhances survival or proliferation, or both, of a neural stem cell among a plurality of target substances includes identifying the active substance using any one of the assay methods previously described.

Any aforementioned Galectin-1 may be a C-S mutant Galectin. As used herein, a "C-S mutant Galectin" refers to a mutant Galectin-1 protein in which at least one cysteine residue among the cysteine residues possessed by Galectin is mutated to a serine residue.

BEST MODE OF CARRYING OUT THE INVENTION

Figure 1:
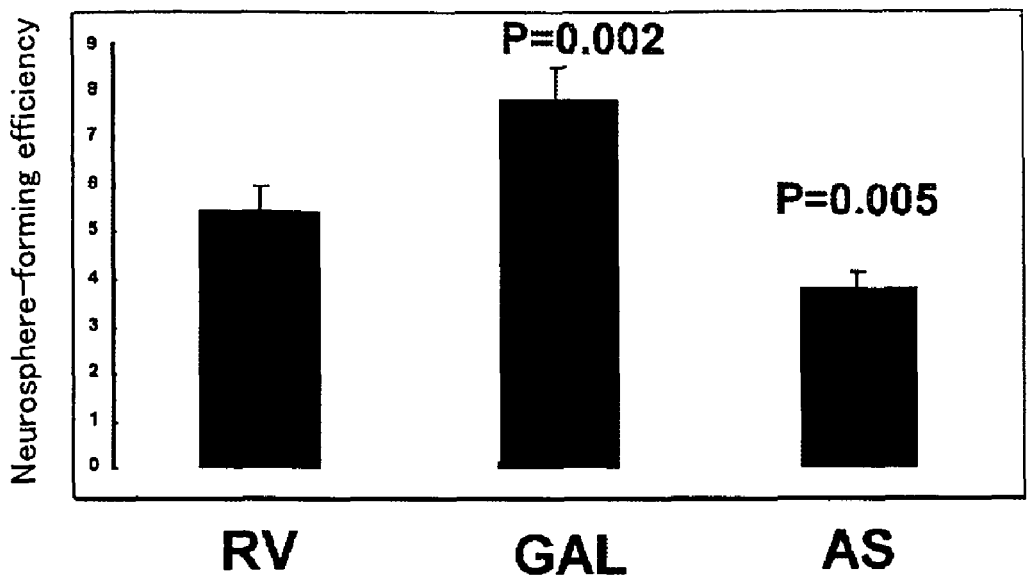
FIG. 1 is a graph showing the neurosphere-forming efficiency when Galectin-1 was forcibly expressed in neural stem cells, together with the control, in Example 2 according to the present invention.

Embodiments of the present invention accomplished based on the above-described findings are hereinafter described in detail. Unless otherwise explained, methods described in standard sets of protocols such as J. Sambrook and E. F. Fritsch & T. Maniatis (Ed.), "Molecular Cloning, a Laboratory Manual (3rd edition), Cold Spring Harbor Press and Cold Spring Harbor, N.Y. (2001); and F. M. Ausubel, R. Brent, R. E. Kingston, D. D. Moore, J. G. Seidman, J. A. Smith, and K. Struhl (Ed.), "Current Protocols in Molecular Biology," John Wiley & Sons Ltd., or alternatively, modified/changed methods from these are used. When using commercial reagent kits and measuring apparatus, unless otherwise explained, attached protocols to them are used.

The objective, characteristics, and advantages of the present invention as well as the idea thereof will be apparent to those skilled in the art from the descriptions given herein. It is to be understood that the embodiments and specific examples of the invention described hereinbelow are to be taken as preferred examples of the present invention. These descriptions are for illustrative and explanatory purposes only and are not intended to limit the invention to these embodiments or examples. It is further apparent to those skilled in the art that various changes and modifications may be made based on the descriptions given herein within the intent and scope of the present invention disclosed herein.

==Overexpression of Galectin in Neural Stem Cells==

The method for enhancing survival or proliferation, or both, of neural stem cells in the liquid medium according to the present invention includes the step of overexpressing Galectin-1 in the neural stem cells. The neural stem cells for use in the present invention are isolated using the neurosphere method of Weiss or its modified methods. Although the animal species or the regions within the central nervous system from which the neural stem cells are derived and the developmental stage of the neural stem cells are not particularly limited, in the following Examples, neural stem cells isolated from forebrain of 14-day mouse embryos were used.

As one example of the method for overexpressing Galectin-1, the Galectin-1 gene may be exogenously introduced and forcibly expressed using a virus vector and a plasmid vector carrying a transcriptional promoter that function in the neural stem cells. As an introduction method, the Galectin-1 gene may be conventionally transfected into the cells. Alternatively, when a virus vector is used as a vector, virus particles carrying the vector may be formed in advance so that the cells may be infected with the virus. Any virus can be used as long as it allows introduction of the Galectin-1 gene into the neural stem cells, enabling forced expression of Galectin-1. For example, adenoviruses, retroviruses, etc. can be used. Not an exogenous gene but an endogenous Galectin-1 locus may be genetically manipulated to enable its overexpression. Specific methods for such manipulation may include replacement of the promoter region of the endogenous Galectin-1 locus with the promoter region of the gene with constitutive expression etc. by homologous recombination and replacement of the structural gene with constitutive expression with the Galectin-1 gene.

Galectin-3, in place of Galectin-1, may be overexpressed in the neural stem cells.

==Addition of Galectin into a Liquid Medium==

As yet another embodiment, Galectin-1 or Galectin-3 may be added into the medium in which neural stem cells are cultured. In this case, Galectin-1 or Galectin-3 is added at a final concentration of preferably more than 100 pg/ml, more preferably more than 100 ng/ml.

Medium containing Galectin-1 may be added instead of purified Galectin-1. For example, the conditioned medium of the OP9 cell line or the neural stem cells may be used. Alternatively, conditioned medium obtained by forced expression of Galectin-1 in a suitable cell line (e.g., the COS cell line, the 293 T cell line, etc.) may be used.

==In Vivo Administration of the Galectin to Mice==

Injection of Galectin-1 or Galectin-3 directly into the brain of a vertebrate in accordance with the present invention can induce neural stem cells and/or SVZ astrocytes intrinsically possessed by an individual to proliferate.

The injection site may be anywhere as long as it is in the brain, but the vicinity of the neural stem cells, e.g., the lateral ventricle, etc., is preferred. The amount of Galectin to be injected is preferably 5 to 100 ng/individual, more preferably 10 to 20 ng/individual. The form of Galectin is not particularly limited, but solution forms in which purified Galectin is dissolved in a culture medium, saline, PBS, etc. are preferred. In that case, it is preferable to add 2-mercaptoethanol and EDTA at 1 to 10 mM and 1 to 5 mM, respectively. Alternatively, the conditioned medium of the OP9 cell line or neural stem cells, or the conditioned medium obtained by forced expression of Galectin-1 in one of the aforementioned suitable cell lines may be used.

Vertebrates to be treated may be humans or animals other than humans. The treatment may be performed on healthy normal individuals or individuals with a neurological disorder, thereby requiring neurotherapy. It is expected that administration of Galectin to normal individuals will improve nerve functions, leading to improvement in the quality of life (QOL). Further, it can be expected that administration of Galectin to patients especially with intractable diseases, such as cerebral ischemia and neural degenerative diseases will enhance regeneration of nerve cells, thereby alleviating or recovering neurological symptoms such as reduced motor function, sensory function, and cognitive function.

==Simultaneous In Vivo Administration of Galectin and Neural Stem Cells to Mice==

The neural stem cells in which Galectin-1 or Galectin-3 is overexpressed, obtained as above, can be used as a therapeutic agent for improving symptoms associated with brain ischemia, especially impaired higher brain function. It is known that higher brain functions that can be impaired by brain ischemia include motor function, sensory function, and cognitive function. In the following Examples, motor function and sensory function are taken as examples of measurement of functional improvement.

When neural stem cells are transplanted, it is preferable to transplant a pharmaceutical composition prepared with a buffer, a career, etc. As is shown in the following Examples, transplantation of the neural stem cells in which Galectin-1 or Galectin-3 is overexpressed produces a more remarkable effect in improving a symptom, as compared with transplantation of ordinary neural stem cells.

As an alternative method for administering Galectin-1 or Galectin-3 in vivo to the brain when neural stem cells are transplanted, Galectin-1 or Galectin-3 may be directly administered into the brain simultaneously with transplantation of neural stem cells, or may be intravenously administered into blood, instead of transplanting neural stem cells in which Galectin-1 or Galectin-3 is overexpressed.

Wild-type Galectin-1 loses its β-galactoside-binding activity within 24 hours in the absence of a reducing agent (e.g., β-mercaptoethanol), whereas C-S Galectin-1 mutants (Galectin-1 mutants such as C2S, C16S, C42S, C60S, C88S, and C130S) retains its activity for over a week. This indicated that for sugar-binding activity to be maintained stable it is important that the cysteine residues are under a reducing condition. (Hirabayashi and Kasai, J Biol Chem 268, 23648-23653). Thus, in a nonreducing condition, C-S Galectin mutants not only has the same β-galactoside-binding activity as wild-type Galectin but also can stably maintain its activity for the longer term than the wild-type Galectin does. In any embodiment of the present invention C-S Galectin mutants may be therefore used in place of the above-mentioned wild-type Galectin. Among C-S Galectin-1 mutants, the C2S mutant is most stable under non-reducing conditions (Hirabayashi and Kasai, J Biol Chem 268, 23648-23653) and is particularly desirable mutant. In addition, C-S Galectin mutants may have a plurality of cysteine residues substituted with serine residues. These mutant proteins are obtainable using the conventional methods by expressing mutant genes obtained by in vitro mutagenesis on the Galectin gene in *E. coli* and purifying the expressed proteins (Hirabayashi and Kasai, J Biol Chem 268, 23648-23653).

==Screening to Identify Active Substances with Activity that Enhances Survival or Proliferation, or Both, of Neural Stem Cells==

According to the present invention, it is possible to assay whether or not a substance to be assayed that has been added in liquid medium has activity that enhances survival or proliferation, or both, of neural stem cells.

First, a basal medium in which neural stem cells are incapable of proliferating when seeded at a clonal density is selected. An assay culture medium is then prepared by adding a substance to be examined to this basal medium and neural stem cells are seeded at a clonal density in the culture assay medium. After culture for a suitable term, it is determined whether or not a substance to be examined has activity that enhances survival or proliferation, or both, of neural stem cells by determining whether or not the seeded neural stem cells are capable of proliferating, i.e., forming colonies in the assay medium.

Neural stem cells to be used may be the cells isolated and induced to proliferate according to the conventional method such as the neurosphere method reported by Weiss et al., but It is preferable to use cells isolated using expression of CD15, a cell surface antigen, as a marker. For example, it is possible to concentrate CD15-expressed cells with techniques such as FACS, the affinity column method, and the magnet bead method using the cells isolated from brains or the cells proliferated by the neurosphere method. Since CD15 is strongly expressed in pluripotent neural stem cells, the neural stem cells can be concentrated several to 10 times or so in the cells to be assayed by this method, producing stable assay results.

To plate the neural stem cells at a clonal density, for example, they may be plated at a low density in one culture plate such that about 10 to 1000 cells are plated in a 10-cm diameter plastic Petri dish. However, it is preferable, for example, to add one cell in one well such that the cells are seeded one by one in each well of a 96-well plastic Petri dish.

As for the basal medium, for example, a liquid medium described in Table 1 of Example 1 or the like can be used; a basal medium can be selected depending on what kind of substance is to be isolated. For example, when a culture medium capable of growing neural stem cells at a high density, but incapable of doing so at a low density, is chosen, the incapability of the neural stem cells to proliferate at low densities can be attributed to lack of factor(s) secreted by the neural stem cells themselves, and the choice will therefore be preferable in assaying various secretory factors secreted by the neural stem cells.

A substance to be assayed may thus be isolated from a liquid medium for neural stem cells etc. and can be purchased from a commercial compound library. Basically any substance can be assayed by the assay method according to the present invention, but substances that do not have toxicity in culture of neural stem cells are preferred.

An assay medium is prepared by adding a target substance to the basal medium thus selected. Neural stem cells in an assay medium can be cultured according to the conventional methods. If the target substance has activity that enhances survival or proliferation, or both, of the neural stem cells after culture for several days to one month, colonies will be observed in the assay medium.

Use of this assay method enables screening for and isolation of substances with activity that enhances survival or proliferation, or both, of neural stem cells among a group of substances such as ones identified from a compound library or a culture medium.

EXAMPLES

The following Examples explain the present invention described so far in more detail, but are not intended to limit the present invention to these Examples.

Example 1 (Preparation of Neurospheres)

Day-14 mouse embryos were removed from day-14 gestation mouse uteri. The peripheral part of the lateral ventricles were isolated and physically dissociated into single cells with a pipet. The cells were plated at the density of $5 \times 10^5$/ml using the liquid medium described in Table 1 and incubated at 37° C. in 5% $CO_2$ for a week, and spheroid floating cell aggregates of about 50-200 μm were obtained.

TABLE 1

|  | /L | Manufacturer and product No. |
|---|---|---|
| DMEM/F12 1:1 | 1.56 g | GIBCO 12400-016 |
| NaHCO3 | 1.2 g (14 mM) | Nacalai |
| Glucose | 2.9 g | Nacalai |
| Transferrin | 100 mg | Wako 208-10333 |
| Insulin | 25 mg | SIGMA I-5500 |
| Progesteron | 6.3 μg | SIGMA P-0130 |
| Sodium Selenate | 5.2 μg | SIGMA S-1382 |
| Putrescine | 9.7 mg | SIGMA P-7505 |
| EGF | 40 μg | Genzyme Tech |
| bFGF | 40 μg | Genzyme Tech |

These cell aggregates were physically dissociated again into single cells and sorted at the cell density of 1 to 100 cells/well in the newly-prepared medium with a cell sorter. At that time, to reduce experimental errors, the sizes of the cells to be sorted were strictly 10 to 25 μm, while dead cells were stained by the PI-staining method and removed. Then, after culture for another seven days, the number of the neurospheres (defined as cell aggregates of 50 μm or more) formed was measured and taken as the forming efficiency. The forming efficiency in this assay system was used as the index of survival and/or proliferation of neural stem cell.

No neurosphere was formed from the cells after sorting according to this method using the liquid medium in Table 1 alone. However, addition of NSF-CM or OP9CM into the culture medium enabled formation of neurospheres after sorting.

OP9CM can be prepared as follows: OP9 cells cultured in αMEM usually containing 20% FCS were washed with PBS several times, supplemented with the medium in Table 1, and incubated for 48 h at 37° C. in 5% $CO_2$. Then, cell components are removed with a 0.45 µm filter to obtain OP9CM.

Example 2 (Forced Expression of Galectin-1)

The full-length of the mouse Galectin-1 cDNA was cloned (GAL) into the retroviral expression vector pMY-IRES-EGFP. The unrecombinant vector (RV) and the recombinant vector with Galectin-1 cDNA inserted in the opposite orientation (AS) were used as the negative controls for the following experiments. These three retroviral vectors and VSV-G expression plasmid were each transfected into the retrovirus-producing cell line 293gp. After incubation for 48 hours, each of the conditioned media was recovered as a retrovirus-containing medium. During incubation of neurospheres according to Example 1, the each of the three retrovirus-containing media were added to the culture medium and only the cells in which infection was established were sorted with the cell sorter. A conditioned medium was used without dilution when cells were sorted. This conditioned medium was prepared by removing cell components through the 0.45 µm filter after 72-hour incubation under the culture condition for the formation of neurospheres.

The forming efficiency (the number of neurosphere/the number of neural stem cells sorted) of neurospheres formed on day 7 was compared among GAL, RV, and AS. The results were as shown in FIG. 1: RV (control) 5.58%, GAL (Galectin-1-forced-expression group) 7.78% (significance level p=0.002), and AS (Galectin-1-antisense-forced-expression group) 3.9% (significance level p=0.005), indicating that forced expression of Galectin-1 enhanced survival and/or proliferation of neural stem cells.

Example 3 (Addition of Galectin-1 or Galectin-3 into the Medium)

Figure 2:
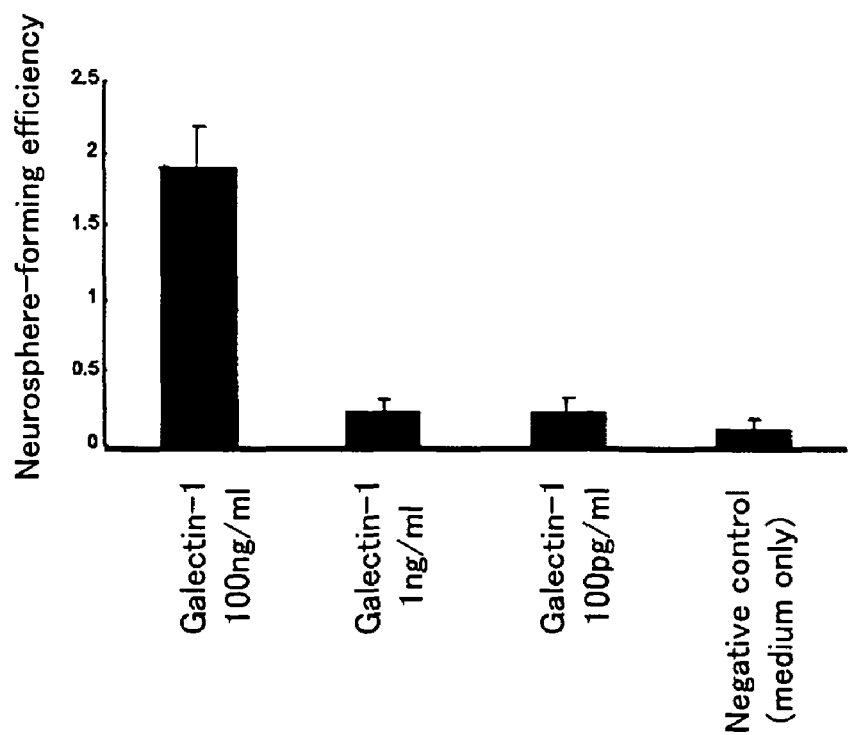
FIG. 2 is a graph showing the neurosphere forming-efficiency when Galectin-1 was added to the medium of neural stem cells, together with the control, in Example 3 according to the present invention.

Recombinant human Galectin-1 (Genzyme Technology) was added at 100 pg/ml, 1 ng/ml, and 100 ng/ml into the culture medium after sorting in Example 1. The results are shown in FIG. 2. In this experiment, the neurosphere-conditioned medium diluted to a final concentration of 66% was used as a culture medium after sorting.

Three independent experiments were performed and the results were as shown in FIG. 2: negative control 0.13%, 100 pg/ml glectin-1 addition 0.23%, 1 ng/ml glectin-1 addition 0.23%, and 100 ng/ml Galectin-1 addition 1.9%, indicating that addition of Galectin-1 at 100 pg/ml or 1 ng/ml increased the neurosphere-forming efficiency and that addition at 100 ng/ml the most markedly increased the neurosphere-forming efficiency. Galectin-1 thus enhanced survival and/or proliferation of neural stem cells depending on its concentration in the medium.

Figure 3:
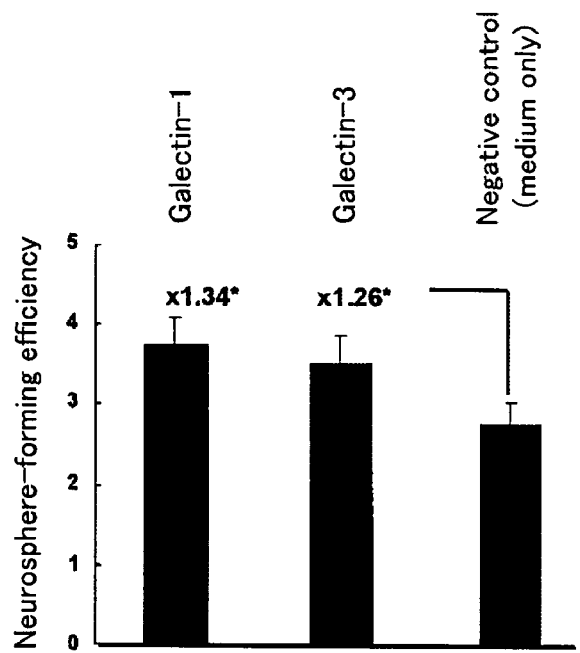
FIG. 3 is a graph showing comparison of the fold neurosphere forming efficiency between when Galectin-3 was added and when Galectin-1 was added into the medium of neural stem cells in Example 3 according to the present invention.

A further experiment was performed using Galectin-3 in place of Galectin-1 at 100 ng/ml (N=5). In this experiment, a neurosphere-conditioned medium was used without dilution as a basal culture medium. The results were as shown in FIG. 3: Galectin-1 addition 3.75% and Galectin-3 addition 3.52%, indicating that Galectin-3 produced an effect similar to that of Galectin-1.

Example 4 (Experiments Using a Model Animal)

==Ischemia Induction of Gerbils==

Sixteen- to twenty-week-old gerbils (*Meriones unguiculatus*) weighing 60 to 76 g were divided into groups of three or four and kept under a 12-hour light/dark cycle. The gerbils were assigned to two groups and anesthetized with 2% isoflurane. Ischemia was induced by pinching the carotid artery with a mini pinchcock for 10 min.

The symptoms of brain infarction were evaluated according to stroke index (SI). That is, a score was assigned as follows to each of the following behaviors or states and the scores of prominent symptoms were summed for each mouse:

| | |
|---|---|
| Hair roughed up or tremor | 1 |
| Obtunded sensation | 1 |
| Paucity of movement | 1 |
| Head cocked | 3 |
| Eye fixed open | 3 |
| Ptosis | 1 |
| Splayed out hind limb | 3 |
| Circling | 3 |
| Fit | 3 |
| Extreme muscular weakness | 6 |

The animals which received a total score of 10 or higher were selected from the ischemia-induced animals. They were subjected to another operation of the ischemia induction five hours after the initial ischemia induction and used for the following transplantation experiment.

==Transplantation of Neural Stem Cells==

Four days after performing the operation of ischemia induction on gerbils, transplantation surgery was performed as follows. Gerbils were anesthetized with 2% isoflurane and placed in a stereotaxic frame. A hole that is large enough for insertion of a 10 µl Hamilton syringe was drilled through the left skull (the same side as used when ischemia was induced) at the position of the caudate nucleus of the corpus striatum at the coordinate (1.0 mm anterior, 1.5 mm lateral, and 1.5 mm ventral) from the bregma when the skull was leveled. Neural stem cells were transplanted into the caudate nucleus by injecting 3 µl of a suspension for transplantation ($5\times10^5$ cells/3 µl) with a Hamilton syringe for more than two minutes, and left for two minutes for their diffusion. Neural stem cells carrying a virus vector (RV) and neural stem cells carrying Galectin-1 (GAL), both of which had been prepared in Example 2, were each transplanted to the two experimental groups. Before transplantation, the neural stem cells were subjected to gene transfer twice in total and incubated for a total of 21 days. To suppress rejection, cyclosporin A (Wako Pure Chemical Industries, Ltd.) mixed with miglyol 812 (Mitsuba Trading Co., Ltd.) was administered to each group of animals three times a week for 4 weeks after surgery. The animals were kept in cages one by one after surgery until feeding, grooming, and weight gain returned to normal.

==Elevated Body Swing Test (EBST)==

To evaluate the motor function of the gerbils used for the experiment, EBST was performed. Each gerbil was held by the base of the tail and elevated about 10 cm above a tabletop. An upper body turn of 10 degrees or higher to either side was defined as the biased swing to that side. The direction and number of the swings for one minute were counted and 3 trials were performed (3 minutes in total) per day. In this experiment, since ischemia had been induced to the left hemisphere of the brain, the percentage of turns made to the side contrary to the left hemisphere, i.e., percent right-biased swing was determined.

Figure 4:
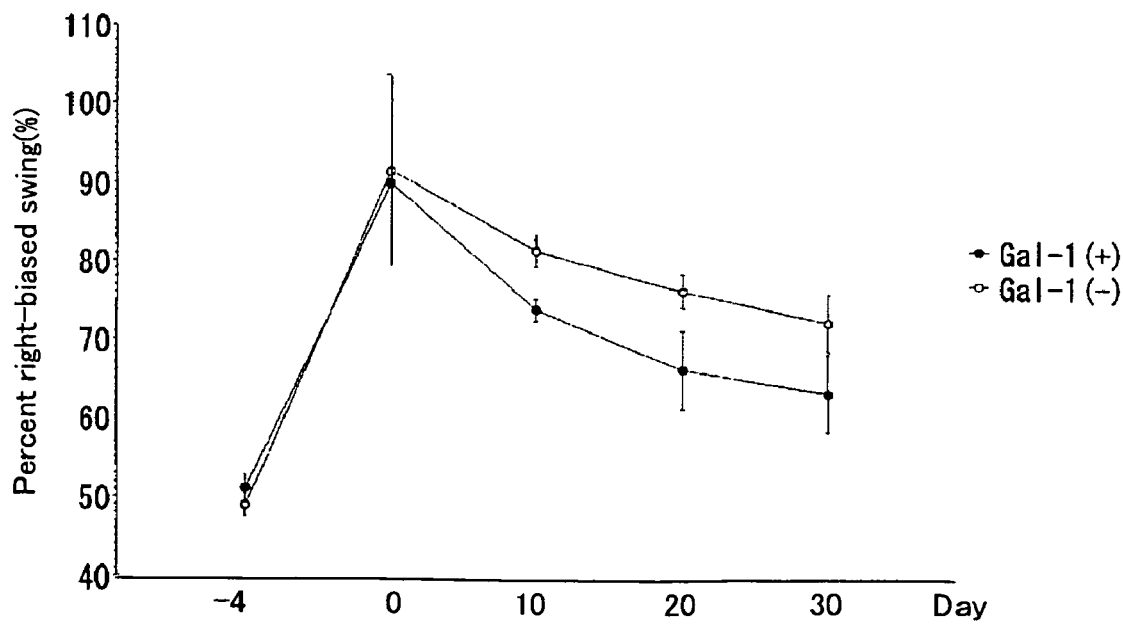
FIG. 4 is a graph showing the results of EBST performed after transplantation of neural stem cells in which Galectin-1 was forcibly expressed (Gal-1$^+$) into gerbils with brain ischemia induced, together with the control (Gal-1$^-$), in Example 4 according to the present invention.

EBST was performed on the day of ischemia induction operation, the day of transplantation of neural precursors, and days 10, 20, and 30 after the transplantation. As shown in FIG. 4, when neural stem cells carrying Galectin-1 (GAL) were used, further recovery of motor dysfunction was observed, compared with neural stem cells carrying virus vector alone (RV).

==Bilateral Asymmetry Test (BAT)==

Next, BAT was performed to evaluate the somatosensory function of the gerbils used for the experiment. In this experiment, unlike Example 2, a lentivirus vector was used. First, total mRNA was isolated from human neurospheres with TRIzol (Invitrogen) and RT-PCR was performed using Superscript2 (Invitrogen) and the following primers. KODplus (TOYOBO) was used as the DNA polymerase. The PCR condition was as follows: an initial denaturation at 94° C. for 2 min followed by 30 cycles of 94° C. for 15 sec, 60° C. for 30 sec, and 68° C. for 60 sec.

Primer 1: GCGGCCGCGCCACCATGGCTTGTG-GTCTGGTCGC (SEQ ID NO: 1)

Primer 2: AGAGTGGATCCTTATCAGTCAAAGGCCA-CACATTTG (SEQ ID NO: 2)

Figure 5:
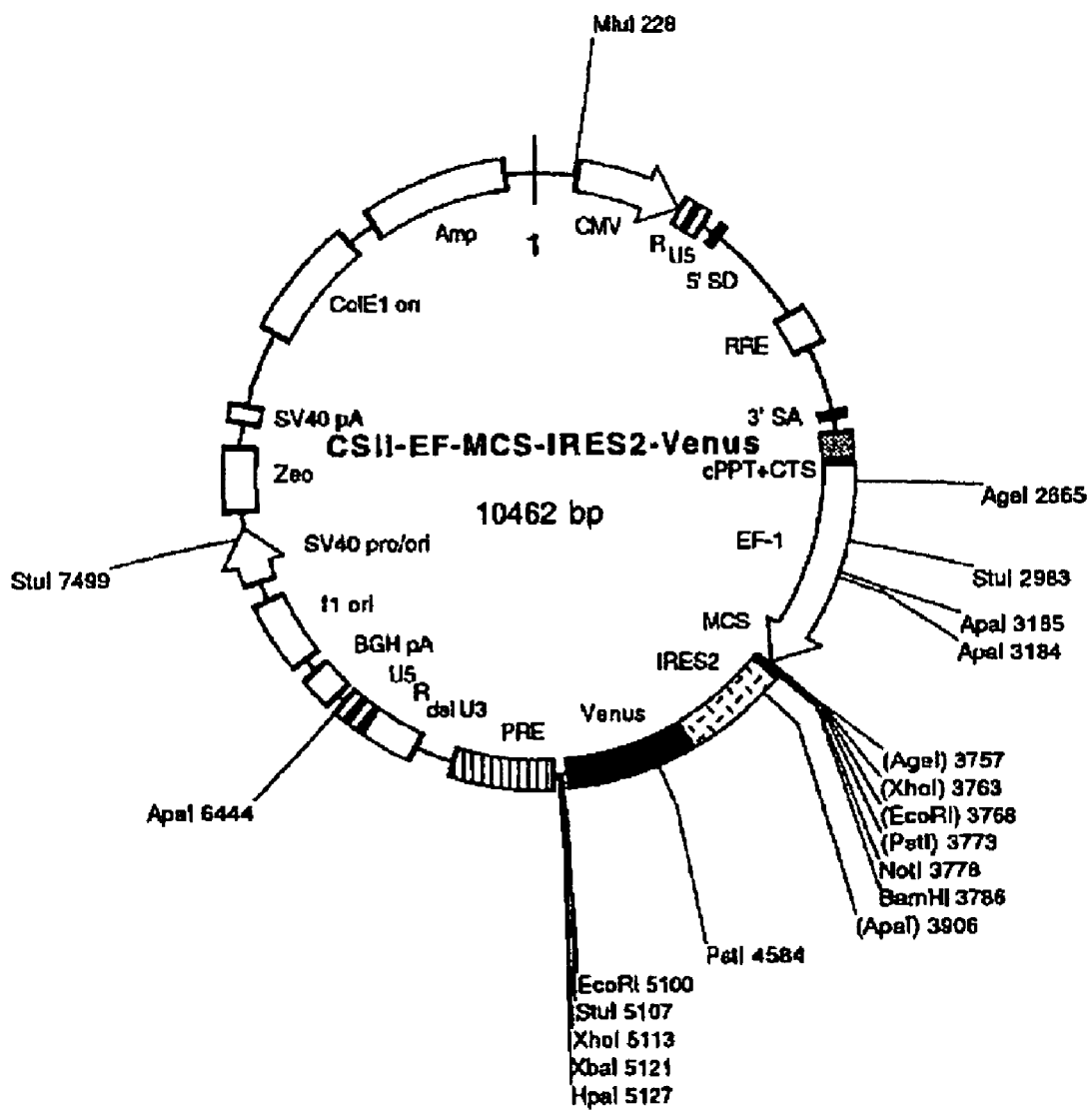
FIG. 5 is a restriction map of the lentivirus vector CSII-EF-MCS-IRES2-Venus used in Example 4 according to the present invention.

The amplified DNA fragment was digested with Not1 and BamH1 and cloned into the Not1-BamH site of CSII-EF-MCS-IRES2-Venus (FIG. 5). Using Galectin-1 expression vector thus obtained, Galectin-1-expressing lentivirus was obtained by the method described in the literature (Miyoshi et al., J. Virol. vol. 72, 8150-8157, 1998). Briefly, a total of four viral component expression plasmids, i.e. the above-mentioned vector, pMDLg/pRRE, pVSV-G, and pRSV-REV, were transfected into 293 T cells and the cells were allowed to produce the virus for a certain period of time. The virus in the medium was purified by ultracentrifuge and allowed to infect the neural stem cells by being added to the medium in which neurospheres are cultured.

A piece of adhesive tape (about 60 mm$^2$) was adhered to the foot of both forelimbs of each gerbil. The time that it took for each gerbil to remove the tape from the foot, i.e. the right foot, on the side contralateral to the ischemic hemisphere was recorded in three trials per day. The average time was used as the score of each animal. The groups and dates of the examination were the same as EBST.

Figure 6:
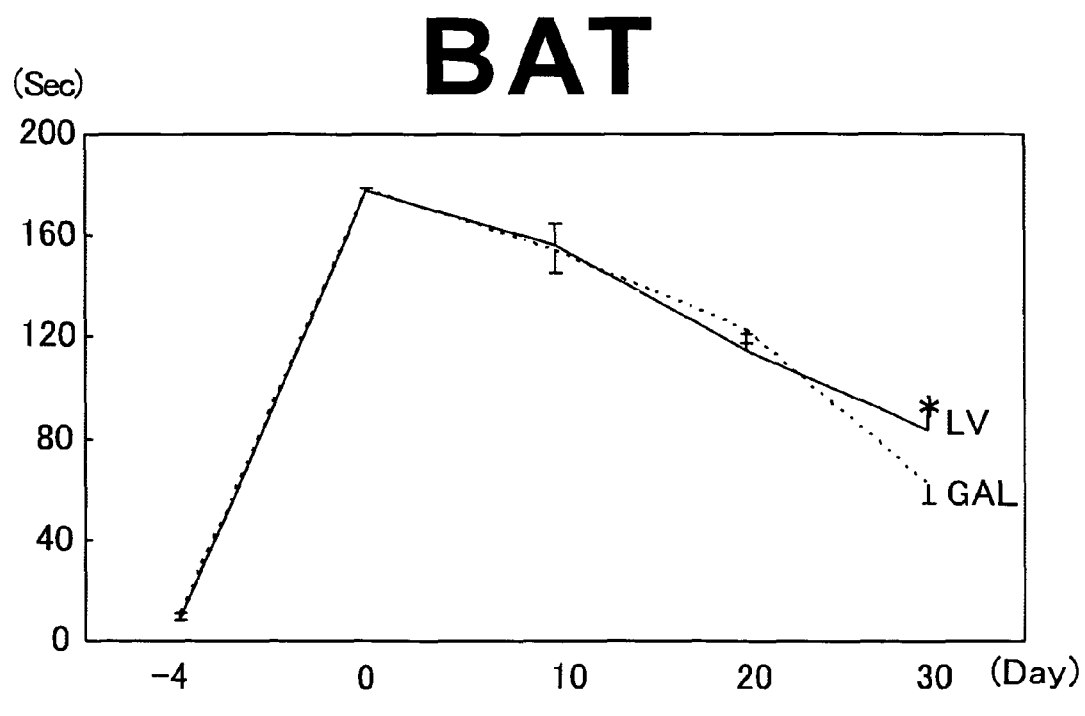
FIG. 6 is a graph showing the results of BAT performed after transplantation of neural stem cells in which Galectin-1 was forcibly expressed (GAL) into gerbils with ischemia induced, together with the control (LV), in Example 4 according to the present invention.

As shown in FIG. 6, when neural stem cells carrying Galectin-1 (GAL) were used, the animals took shorter time to remove the tape, compared with neural stem cells carrying virus vector alone (RV) were used. Recovery of sensory nerve dysfunction was thus observed.

Example 5 (Neurite Extension Effect of Nervous Cells of the Central Nervous System)

Figure 7:
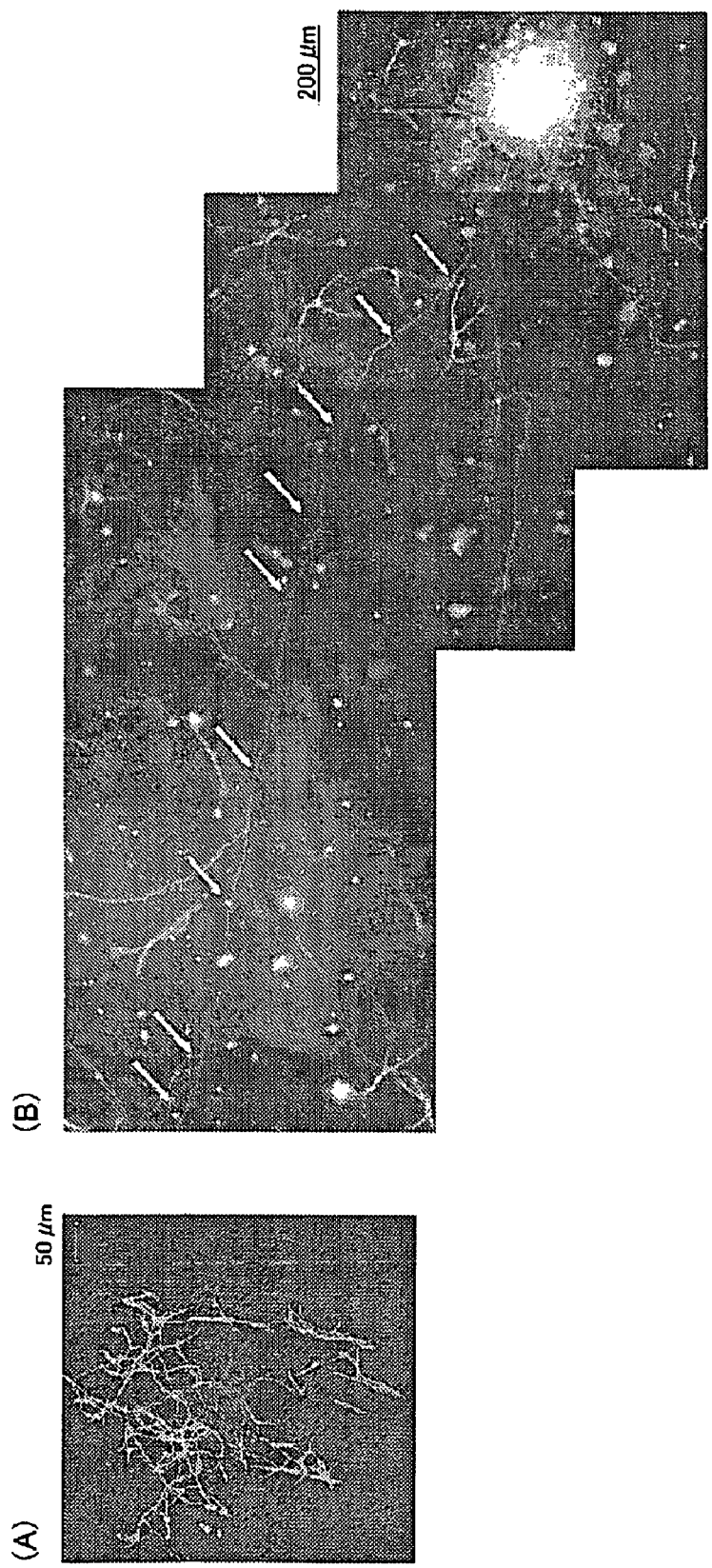
FIG. 7 is photographs showing untreated neural stem cells (A) and neural stem cells in which Galectin-1 is forcibly expressed (B), both of which differentiated and were subsequently were subjected to antibody staining using anti-betaIII-tubulin antibody in Example 5 according to the present invention. The arrows show extended neurites.

The neural stem cells carrying the retroviral vector pMY-IRES-EGF into which mouse Galectin-1 cDNA had been introduced, prepared in Example 2, were allowed to differentiate into neurons by removing growth factors EGF and FGF from the culture medium and culturing the cells in adhesion to the culture dish. The differentiated cells were stained with βIII-tubulin, a neuronal-specific marker. It was found, as shown in FIG. 7, that nerve cells into which Galectin-1-expressing neural stem cells had differentiated had markedly extended neurites, compared with nerve cells (control) into which untreated neural stem cells had differentiated.

Example 6 (Effect of Galectin-1 Injection into Mice)

==Increase in Neurosphere-Forming Ability by Galectin-1 Injection==

Mouse Galectin-1 was dissolved in 0.9% saline. A solution containing a total amount of 14 µg of mouse Galectin-1 and a solution without mouse Galectin-1 were each injected into the lateral ventricle of one hemisphere (Ipsi.) of mice (10 to 15 weeks of age) at a rate of 0.5 µl with an osmotic pump for seven days, whereas nothing was injected into the lateral ventricle of the other hemisphere (Ctra.) of the same mice. The experimental results were thus compared among four sites: the ipsilateral side to Galectin-1 injection (Ipsi. Gal-1), the contralateral side to Galectin-1 injection (Contra. Gal-1), the ipsilateral side to saline injection (Ipsi. Saline), and the contralateral side to saline injection (Ctra. Saline).

Figure 8A:
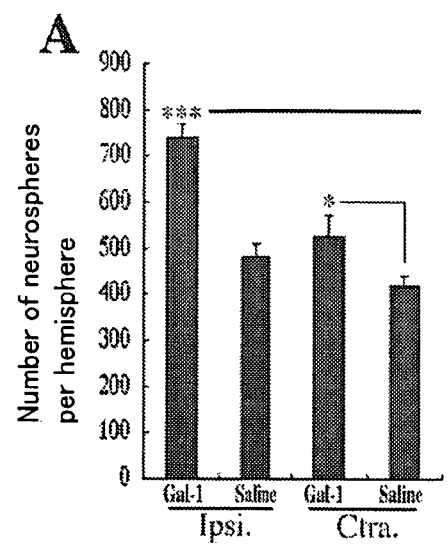
In FIG. 8, (A) is a graph showing the total number of primary neurospheres formed from neural stem cells isolated from brains injected with Galectin-1 in Example 6 according to the present invention (Ipsi: neurospheres obtained from the brain hemisphere ipsilateral to the injected hemisphere; Ctra: neurospheres obtained from the brain hemisphere contralateral to the injected hemisphere); (Gal-1: brains of animals injected with Galectin-1; Saline: brains of animals injected with saline); (B) is photographs showing the results of examination of the cell proliferation ability in the SVZ of brains injected with Galectin-1 in Example 6 according to the present invention. (C) is a graph showing the number of signals on a plurality of sections.

Tissues in the vicinity of the lateral ventricle in both hemispheres from the brain tip to the crossing of the ventricle on the left and right hemispheres were isolated with care to avoid contamination of the cortical layer or the hippocampus, and each tissue was dissociated into single cells. Dissociated cells were plated in six-well dishes at a concentration of 1000 to 2000 cells/ml using the above-mentioned medium containing 20 ng/ml EGF. On days 10 to 12 of culture, the total number of primary neurospheres formed was counted. The results are shown in FIG. 8A.

When Galectin-1 (Ipsi., Gal-1) was injected, the number of neurospheres that can be obtained per hemisphere was significantly increased, compared with the case in which saline (Ipsi., Saline) was injected. This increase was also observed in the hemisphere on the non-injected sides (Ctra.) (Gal-1 vs. Saline).

Not less than 99% of neurospheres obtained from Galectin-injected mice exhibited formation of secondary neurospheres or pluripotency into neurons and glia.

These results suggest that Galectin-1 increases the number of neural stem cells, thereby indicating that injection of Galectin-1 has the effects of enhancing survival or proliferation in vivo, or both, of neural stem cells in mice.

==Enhancement of Cell Proliferation Ability in the SVZ by Galectin-1 Injection==

In this Example, it was investigated whether or not cell proliferation ability in the subventricular zone (SVZ) is enhanced when Galectin-1 is injected into the mouse brain. The SVZ is the region where it is known that nerve cell proliferation is still continuing even in the adult brain.

Figure 8B:
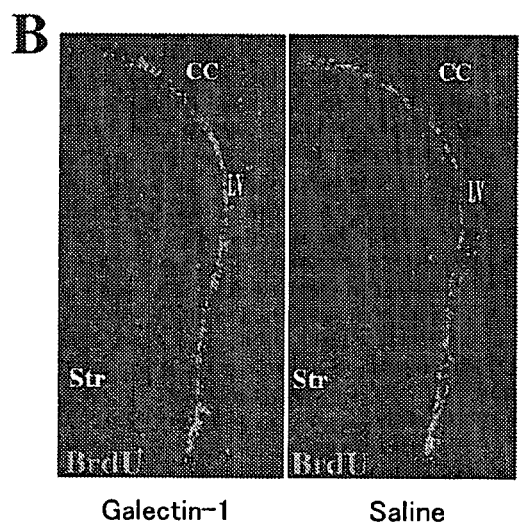
Figure 8C:
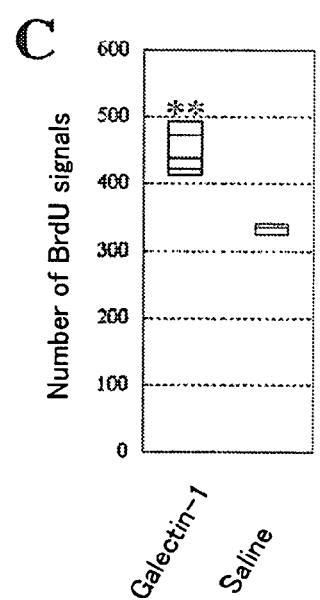

After injection of Galectin-1 into the brains of mice (eight weeks of age) for seven days, the mice were intraperitoneally injected with a BrdU solution (Sigma Chemical Corporation) dissolved in 0.007% NaOH in phosphate buffer every 2 hours for 10 hours at a final concentration of 120 mg/kg bw. Thirty minutes after the last administration, the mice were subjected to perfusion fixation with 4% formaldehyde solution. The brains were isolated and further post-fixed overnight in 4% formaldehyde solution. Sections of 50 µm were made with a vibratome. The sections were then rinsed three times with PBS and incubated with TNB blocking solution (Vector Laboratories) for 1 hour. After overnight incubation at 4° C. with anti-BrdU antibody (rat monoclonal, Abcam Ltd., 1:100), the sections were further incubated for one hour at room temperature with a biotinylated secondary antibody (Anti-Rat IgG, 1:200). The sections were then rinsed in PBS and color was developed using ABC Elite Kit (Vector Laboratories). The results are shown in FIG. 8B, together with the results in the animals injected with saline. In addition, the results of counting the number of cells with their nucleus stained with anti-BrdU antibody on a plurality of slices of the SVZ are shown in FIG. 8C.

When Galectin-1 was injected, the number of cells with their nucleus stained was on a 36% increase on average, compared with the case in which saline was injected. No significant difference was found in the number of cells undergoing apoptosis among these samples (figure not shown). These results suggest that Galectin-1 has the effect of enhancing in vivo proliferation of neural stem cells in mice.

==Increase in the Number of Cells Constituting SVZ by Galectin-1 Injection==

As so far described, injection of Galectin-1 enhanced cell proliferation in the SVZ. It was further investigated whether or not such enhancement would increase the number of cells constituting the SVZ.

It is known that in the SVZ, a part of SVZ astrocytes function as stem cells, differentiate into transit amplifying cells (TA cells) at the mid-stage of differentiation, proliferate again, and differentiate into neuroblasts (NBs). Thus, to identify cell types, cells constituting the SVZ are stained with various cell markers, using the sections of the mice injected with Galectin-1 and BrdU as mentioned above.

Figure 9:
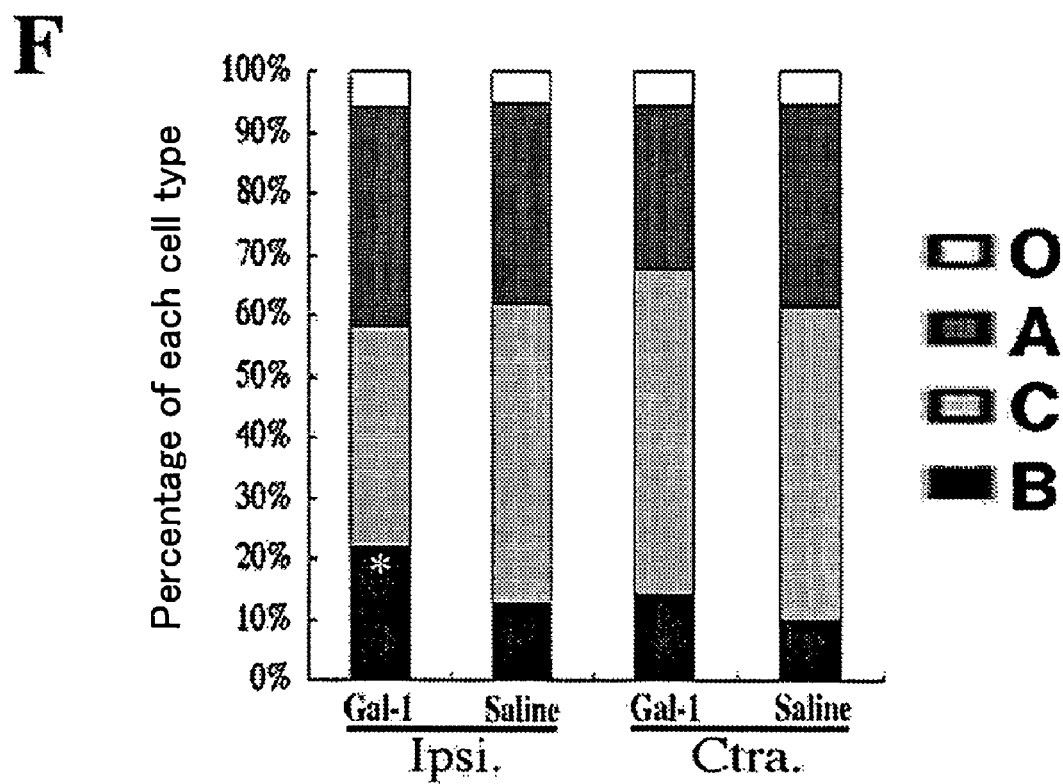
FIG. 9 is a graph showing the changes in percentage of cells constituting the SVZ, caused by Galectin-1 injection Example 6 according to the present invention.

Here, proliferating cells were stained with BrdU. Simultaneously, histochemistry staining was performed using a rabbit anti-Dlx antibody (used at a 1:400 dilution; provided from Ms. Grace Panaganiban), a mouse anti-Mash1 monoclonal antibody (used at a 1:100 dilution; Phaemingen), and rabbit anti-Sox21 antibody (used at a 1:10 dilution; made by the present inventors) (Ohba et al., Neurosci Lett. 358 (3):157-60, 2004). Anti-Dlx antibody is specifically recognizes TA cells and NBs. Anti-Mash1 antibody recognizes a subset of Dlx$^+$ cells. Since almost all cells in this subset are BrdU-positive, and GFAP- and PSA-NCAM-negative, it follows that anti-Mash1 antibody specifically recognizes the whole or part of TA cells. Anti-Sox21 antibody recognizes all the SVZ cell strains. Histochemistry staining was performed by the same technique used for the above-mentioned anti-BrdU antibody. The results are shown in FIG. 9 and Table 2.

These results showed that injection of Galectin-1 enhances in vivo proliferation of SVZ astrocytes in mice. Since a part of SVZ astrocytes function as neural stem cells, these results support that injection of Galectin-1 enhances in viva proliferation of neural stem cells in mice.

==Increase in the Number of Slowly Proliferating Cells by Galectin-1 Administration==

It is known that neural stem cells are contained in a group of cells slowly proliferating in vivo. Thus, it was investigated whether or not injection of Galectin-1 enhances in viva proliferation of slowly proliferating cells in mice.

Figure 10:
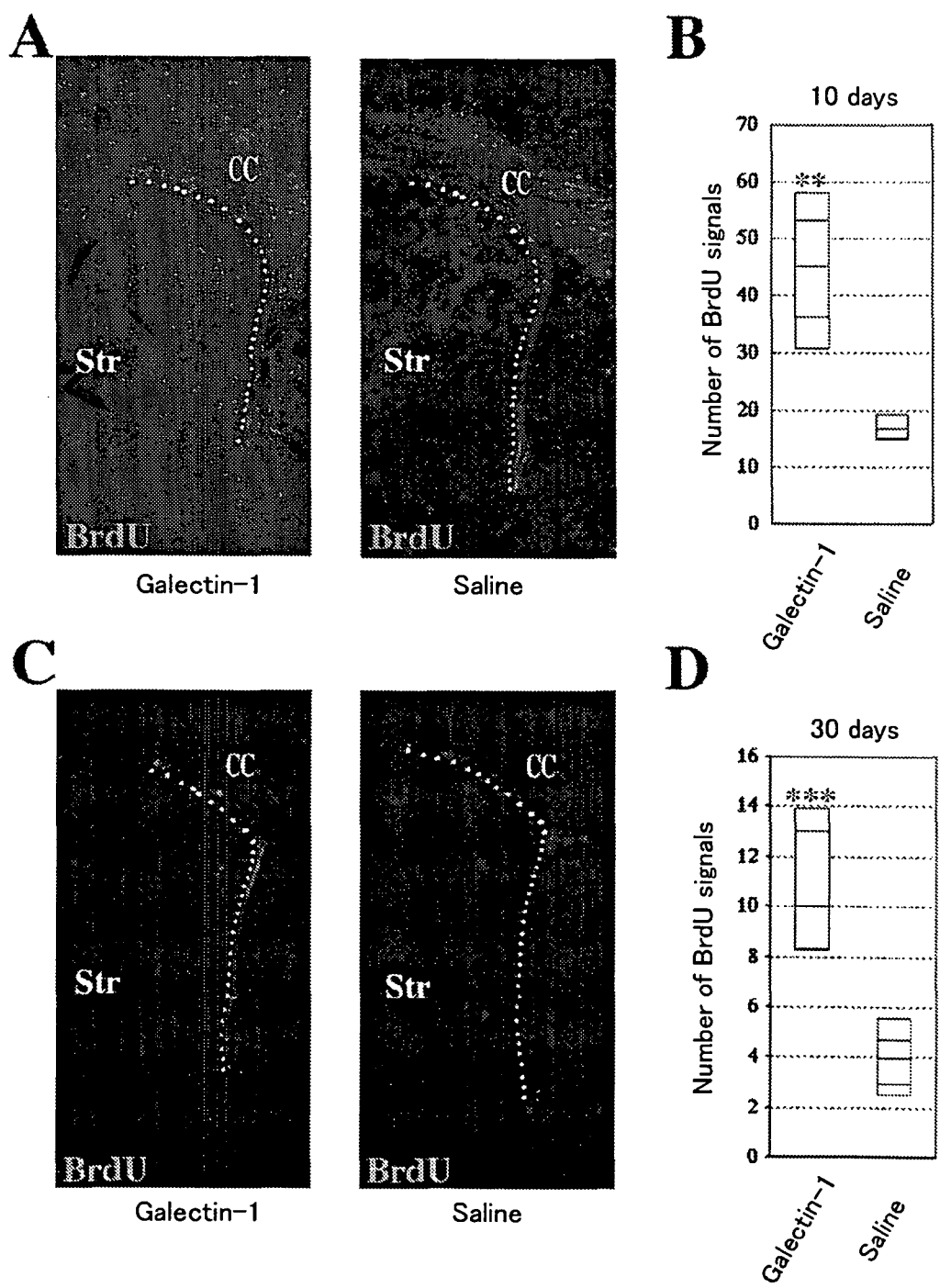
FIG. 10 shows the results of examination on whether or not Galectin-1 injection enhances in vivo proliferation of slowly proliferating cells in the mouse brain in Example 6 according to the present invention. Mice were dissected and their brains isolated 10 days (A and B) and 30 days (C and D) after the last day of Galectin-1 injection. Here, A and C are photographs showing the results of examination of the cell proliferation ability of slowly proliferating cells in the SVZ of the brain in Example 6 according to the present invention; B and D are graphs showing the numbers of signals on a plurality of sections in A and C, respectively.

In this experiment, mice were provided with water supplemented with 1 mg/ml BrdU for seven days, instead of receiving an intracerebral injection of BrdU. The mice were dissected and their brains were isolated 10 and 30 days after the last day of Galectin-1 injection. BrdU was detected in the same manner as described above. The results are shown in FIG. 10.

In the brains injected with Galectin-1, the number of BrdU-positive cells significantly (on day 10: p=0.01, day 30: p<0.001) increased compared with the brains injected with saline. However, no significant difference was found in the percentage of cells in which Mash1 that recognizes a subset of TA cells is expressed in BrdU-positive cells between the Galectin-1-injection group and the control group (figure not shown). These results revealed that injection of Galectin-1 enhances in vivo proliferation of slowly proliferating cells before differentiation into TA cells in mice. This conclusion supports that injection of Galectin-1 enhances in vivo proliferation of neural stem cells in mice.

INDUSTRIAL APPLICABILITY

According to the present invention, methods for enhancing survival and/or proliferation of neural stem cells and pharmaceutical compositions containing neural stem cells, prepared by such methods, can be provided. In addition, in vertebrates, neural stem cell proliferation enhancers and SVZ astrocyte proliferation enhancers for enhancing in vivo proliferation of

TABLE 2

Galectin-1 increases NSPCs in the adult SVZ

|  |  | SVZ astrocytes | TA cells | Neuroblasts |
|---|---|---|---|---|
| Marker | Sox21 | + | + | + |
|  | Dlx | − | + | + |
|  | Mash1 | − | + | − |
| Number of cells | Galectin-1 | 65.0 +/− 13.0* | 236 +/− 18.7* | 125 +/− 37.2 |
|  | Saline | 32.6 +/− 4.15 | 171 +/− 11.1 | 109 +/− 9.20 |
| Relative ratio | Galectin-1/saline | 1.99 | 1.38 | 1.14 |

FIG. 9 is a graph showing the percentage of cells detected under each experimental condition (A: NB cells Dlx$^+$/Mash1$^-$, B: SVZ astrocytes BrdU$^+$/Sox21$^+$/Dlx$^-$, C: TA cells Mash1$^+$, and O: other cells). These results indicate that injection of Galectin-1 significantly (p<0.05) increased the percentage of proliferating SVZ astrocytes (B; the part marked with an asterisk in the graph). Injection of Galectin-1 also significantly (p<0.05) increased the percentage of proliferating SVZ astrocytes (B) on the hemisphere contralateral to the Galectin-1 injection. In addition, Table 1 shows that the number of not only SVZ astrocytes (B) but also TA cells (C) significantly increased.

neural stem cells or SVZ astrocytes, together with methods for enhancing in vivo proliferation of neural stem cells and methods for enhancing in vivo proliferation of SVZ astrocytes for enhancing in vivo proliferation of neural stem cells or SVZ astrocytes can be provided.

Moreover, assay methods for assaying activity that enhances survival or proliferation, or both, of neural stem cells, together with a screening method for screening for substances with activity that enhances survival or proliferation, or both, of neural stem cells can be provide.

The invention claimed is:

1. A method for enhancing in vivo proliferation of neural stem cells in a vertebrate, comprising administering an effective amount of Galectin-1 to the brain of the vertebrate, wherein administration of the effective amount of Galectin-1 enhances proliferation of neural stem cells.

2. The method of claim 1, wherein the vertebrate is normal.

3. A method for enhancing in vivo proliferation of subventricular zone (SVZ) astrocytes in a vertebrate, comprising administering an effective amount of Galectin-1 to the brain of the vertebrate, wherein administration of the effective amount of Galectin-1 enhances proliferation of SVZ astrocytes.

4. The method of claim 3, wherein the vertebrate is normal.

5. The method of claim 3, wherein the Galectin-1 is a C-S mutant Galectin-1 in which at least one cysteine residue among the cysteine residues possessed by Galectin-1 is mutated to a serine residue.

6. The method of claim 1, wherein the vertebrate has a neurological disorder.

7. A method for treating a patient with a neurological disorder, comprising enhancing in vivo proliferation of neural stem cells in the patient by administering an effective amount of Galectin-1 to the brain of the patient, wherein administration of the effective amount of Galectin-1 enhances proliferation of neural stem cells.

8. The method of claim 7, wherein the neurological disorder is cerebral ischemia or a neural degenerative disease.

9. The method of claim 1, wherein the Galectin-1 is a C-S mutant Galectin-1 in which at least one cysteine residue among the cysteine residues possessed by Galectin-1 is mutated to a serine residue.

10. The method of claim 3, wherein the vertebrate has a neurological disorder.

11. A method for treating a patient with a neurological disorder, comprising enhancing in vivo proliferation of SVZ astrocytes in the patient by administering an effective amount of Galectin-1 to the brain of the patient, wherein administration of the effective amount of Galectin-1 enhances proliferation of SVZ astrocytes.

12. The method of claim 11, wherein the neurological disorder is cerebral ischemia or a neural degenerative disease.

* * * * *

UNITED STATES PATENT AND TRADEMARK OFFICE
CERTIFICATE OF CORRECTION

| | | |
|---|---|---|
| PATENT NO. | : 7,785,596 B2 | Page 1 of 1 |
| APPLICATION NO. | : 10/571277 | |
| DATED | : August 31, 2010 | |
| INVENTOR(S) | : Hideyuki Okano et al. | |

It is certified that error appears in the above-identified patent and that said Letters Patent is hereby corrected as shown below:

On the Title Page, Item (54), in the Title, line 3-4, "EXTENSION ENHANCERS" should read --EXTENSION, ENHANCERS--;

line 4-5, "THEREFOR PHARMACEUTICAL" should read
--THEREFOR, PHARMACEUTICAL--;

line 6, "CELLS ASSAY" should read --CELLS, ASSAY--; and line 7, "METHODS AND" should read --METHODS, AND--.

Signed and Sealed this
Twenty-eighth Day of December, 2010

David J. Kappos
*Director of the United States Patent and Trademark Office*